United States Patent [19]

Gennari

[11] Patent Number: 5,047,405

[45] Date of Patent: Sep. 10, 1991

[54] ANTIAMNESIC USE OF PTERIDINE DERIVATIVES

[75] Inventor: Federico Gennari, Truccazzano, Italy

[73] Assignee: Bioresearch S.p.A., Milan, Italy

[21] Appl. No.: 488,438

[22] Filed: Feb. 27, 1990

Related U.S. Application Data

[63] Continuation of Ser. No. 182,726, Apr. 18, 1988, abandoned.

[30] Foreign Application Priority Data

May 14, 1987 [IT] Italy ........................... 20516 A/87

[51] Int. Cl.⁵ .................... C07D 57/28; A61K 31/505
[52] U.S. Cl. ..................................... 514/249; 544/257
[58] Field of Search .......................... 544/257; 514/249

[56] References Cited

U.S. PATENT DOCUMENTS 3,895,012  7/1975  Liede et al. ........................ 544/257
4,183,934  1/1980  Paris et al. ........................ 514/249

Primary Examiner—Mukund J. Shah
Assistant Examiner—Matthew V. Grumbling
Attorney, Agent, or Firm—Parkhurst, Wendel & Rossi

[57] ABSTRACT

Pteridines of general formula (I):

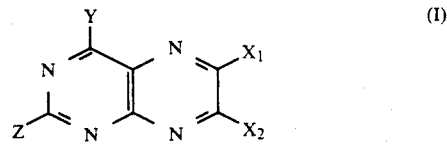

in which Y and Z, which can be identical or different, are hydrogen, OH or $NH_2$, and $X_1$ and $X_2$, which can be identical or different, are hydrogen, OH, $C_1$–$C_4$ alkyl, phenyl, hydroxymethyl or carboxyl, for the preparation of pharmaceutical compositions for treating cognitive pathologies characterized by memory and vigilance disturbances, such as senile dementia of Alzheimer type, multiinfarctual dementia, metabolic encephalopathies, Korsakoff's syndrome, and the consequences of the abuse of certain therapies such as anxiolytic and neuroleptic.

4 Claims, No Drawings

ANTIAMNESIC USE OF PTERIDINE DERIVATIVES

This is a continuation of application Ser. No. 07/182,726 filed Apr. 18, 1988, now abandoned.

This invention relates to pteridines suitable for the preparation of compositions with antiamnesic activity.

More particularly, the invention relates to the use of pteridines of the following general formula:

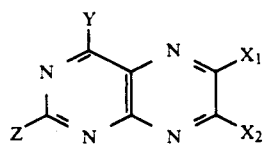
(I)

in which Y and Z, which can be identical or different, are hydrogen, OH or $NH_2$, and $X_1$ and $X_2$, which can be identical or different, are hydrogen, OH, $C_1$-$C_4$ alkyl, phenyl, hydroxymethyl or carboxyl, for the preparation of compositions with antiamnesic activity.

The invention also relates to a process for preparing pteridines of general formula (I).

The pteridines are a class of substances present in numerous living species ranging from the invertebrates and birds to higher mammals including man. They can also be prepared synthetically.

Their biological significance and their participation in many enzymatic reactions have not yet been completely clarified, even though they have been the subject of numerous studies [H. Rembold and W. L. Gyure, Angew. Chem. Internat. Edit. vol II (1972), No. 12, pp 1061, 1072].

We have now surprisingly found that natural or synthetic pteridines of general formula (I) demonstrate activity of positive nootropic type in a test traditionally used in selecting molecules of antiamnesic activity, namely the test of activity towards amnesia induced by electroshock treatment.

Said test, as described by Butler et al. (J. Medicinal Chem. 27, 684, 1984), enables the activity of products able to antagonise retrograde amnesia induced by electroconvulsive shock in the mouse to the evaluated.

It consists of the following operations:

(a) conditioning the animal to avoid entering, in a single attempt, a dark chamber in which it would receive an electric shock in its paws (passive avoidance);

(b) induce retrograde amnesia by electroshock treatment;

(c) administer the products under examination to the animal;

(d) evaluate the persistance or non-persistance of the conditioning as an index of the absence or, respectively, presence of the amnesia.

The percentage of animals showing retention of the condition after introduction of the amnesia is an index of the antiamnesic activity of the product under examination.

Table 1 shows the results of the use of pteridines of formula (I) in the aforesaid test, showing the percentages of inversion of the amnesia at various doses compared with the control group not subjected to electroshock treatment.

The dose-effect curve is bell-shaped, i.e. increasing the dose first causes an increase in the effect and then a decrease therein. This pattern is typical of products which influence the cognitive functions.

The greatest effect was observed in the tests at an orally administered dose of 2.5 mg/kg with the products BR 474 and BR 467. In these tests the amnesic action of the electroshock treatment is practically nullified, as demonstrated by the fact that the percentages of animals retaining the conditioning are entirely similar to the control group percentages not subjected to electroshock treatment.

The products were administered orally 90 minutes before evaluating the retention of the conditioning.

Those animals which did not enter the conditioning chamber within 60 seconds were considered amnesia-free.

TABLE 1

| No. | CODE | Pteridines of formula (I) | Y | Z | $X_1$ | $X_2$ | % AMNESIA INVERSION Dose mg/kg/os 1.25 | 2.5 | 5 |
|---|---|---|---|---|---|---|---|---|---|
| 1 | BR 482 | 2-amino-4,6,7-trihydroxy pteridine (leucopterin) | OH | $NH_2$ | OH | OH | 31.6 | 86.3 | 31.6 |
| 2 | BR 483 | 2-amino-4,6-dihydroxy pteridine (xanthopterin) | OH | $NH_2$ | OH | H | 9.0 | 20.6 | 20.6 |
| 3 | BR 465 | 2-amino-4-hydroxy-6-methylpteridine | OH | $NH_2$ | $CH_3$ | H | 37.5 | 65.9 | 57.9 |
| 4 | BR 466 | 2-amino-4-hydroxy-7-methylpteridine | OH | $NH_2$ | H | $CH_3$ | 38.1 | 55.7 | 42.2 |
| 5 | BR 476 | 2-amino-4-hydroxy-6-phenylpteridine | OH | $NH_2$ | $C_6H_5$ | H | 24.9 | 57.9 | 16.9 |
| 6 | BR 477 | 2-amino-4-hydroxy-7-phenylpteridine | OH | $NH_2$ | H | $C_6H_5$ | 31.7 | 72.7 | 18.1 |
| 7 | BR 464 | 2-amino-4-hydroxy-6-hydroxymethylpteridine | OH | $NH_2$ | $CH_2OH$ | H | 21.5 | 31.8 | 31.8 |
| 8 | BR 469 | 2-amino-4-hydroxy-6-carboxymethylpteridine | OH | $NH_2$ | COOH | H | 9.0 | 18.1 | 0 |
| 9 | BR 468 | 2-amino-4-hydroxy-pteridine | OH | $NH_2$ | H | H | 54.6 | 57.2 | 57.2 |
| 10 | BR 467 | 2-amino-4-hydroxy-6,7-dimethylpteridine | OH | $NH_2$ | $CH_3$ | $CH_3$ | 50.3 | 100.0 | 71.5 |
| 11 | BR 474 | 2,4-diamino-6,7-dimethyl pteridine | $NH_2$ | $NH_2$ | $CH_3$ | $CH_3$ | 12.4 | 102.6 | 71.6 |
| 12 | BR 470 | 2-amino-6,7-dimethyl pteridine | H | $NH_2$ | $CH_3$ | $CH_3$ | 59.0 | 59.0 | 37.4 |
| 13 | BR 471 | 2,4-hydroxy-6,7-dimethyl pteridine | OH | OH | $CH_3$ | $CH_3$ | 50.8 | 75.4 | 63.3 |

TABLE 1-continued

| No. | CODE | Pteridines of formula (I) | Y | Z | $X_1$ | $X_2$ | % AMNESIA INVERSION Dose mg/kg/os 1.25 | 2.5 | 5 |
|---|---|---|---|---|---|---|---|---|---|
| 14 | BR 472 | 4-hydroxy-6,7-dimethyl pteridine | OH | H | $CH_3$ | $CH_3$ | 25.0 | 56.8 | 25.0 |

The pharmacological results obtained in the test demonstrate the effectiveness of the pteridines according to the invention in reducing experimentally induced amnesia and thus the importance of their use in the treatment of cognitive pathologies characterised by memory and vigilance disturbances which are encountered in old age, in some pathologies such as senile dementia of Alzheimer type, multiinfarctual dementia, metabolic encephalopathies and Korsakoff's syndrome, and as a consequence of the abuse of certain therapies (anxiolytic, neuroleptic).

Said pteridines can be used for preparing both injectable forms and oral formulations such as tablets, pills, delayed release capsules, gastroresistant tablets, sachets, syrups, extemporaneous syrups, delayed release syrups and other forms normally used in pharmaceutics.

The pteridines of formula (I) are known products which can be prepared by various methods, such as the method described by C. B. Storm et al., in J. Org. Chem., 36, 3925 (1971).

Advantageously, pteridines of formula (I) are prepared by the process of the present invention, which is based on condensing suitable amino derivatives of pyrimidine with suitable dicarbonyl compounds, in an aqueous medium in the presence of sodium sulphite, at controlled pH.

The process for preparing pteridines of formula (I) according to the present invention is characterized by the following stages of implementation:

(a) adding an aqueous suspension of a pyrimidine amino derivative to a mixture formed from a dicarbonyl compound and an aqueous sodium sulphite solution of pH between 7 and 8;

(b) condensing the pyrimidine derivative with the dicarbonyl compound at controlled pH between 7 and 8;

(c) filtering off the precipitate and redispersing it in distilled water;

(d) dissolving it by alkaline or acid treatment;

(e) treating with activated carbon;

(f) crystallizing.

These and further characteristics of the process according to the invention will be more apparent from the detailed description given hereinafter of some preferred embodiments of the process.

Said pyrimidine amino derivative is for example: 2,4,5-triamino-6-hydroxypyrimidine, 2,4,5,6-tetraaminopyrimidine, 4,5,6-triamino-pyrimidine, 5,6-diamino-2,4-dihydroxypyrimidine, 4,5-diamino-6-hydroxypyrimidine and the like, and said dicarbonyl compound is for example diacetyl-(2,3-butanedione), glyoxal and the like.

The pyrimidine amino derivative is finely ground to below 200 microns and suspended in distilled water to the extent of 10-20 kg/100 liters.

Separately, a solution of $Na_2SO_3$ in distilled water is prepared with a concentration of 5-20 kg/100 liters. This solution is treated with 6N HCl to adjust the pH to between 7 and 8, after which the dicarbonyl compound is added to the extent of 1-3 kg/100 liters of solution, controlling the pH at between 7 and 8 by adding 6N HCl.

The pyrimidine amino derivative suspension is added to this solution in a volume ratio of 1:3-1:5, under agitation, while controlling the pH at between 7 and 8 by adding a NaOH solution, and the reaction is effected at a temperature of between ambient and 70° C. for 1-2 hours.

The formed precipitate is recovered by filtration, washed with distilled water, redispersed in distilled water to the extent of 1.5-4 kg/100 liters and dissolved by treating with $Na_2CO_3$ or HCl at a temperature of between ambient and the solution boiling point, according to the type of compound prepared.

The solution is clarified by treatment with activated carbon, the solution pH corrected to 8-9 and crystallization carried out at a temperature of 4°-20° C., the pH correction being done by adding 6N HCl or 40% NaOH according to the solution characteristics.

The following examples illustrate the process for preparing certain pteridines according to the invention, but these examples are given for the purpose of non-limiting illustration only.

Some examples are also given of the preparation of compounds containing said pteridines for antiamnesic use.

EXAMPLE 1

Preparation of 2-amino-4-hydroxy-6,7-dimethyl pteridine (BR 467)

10 kg of anhydrous sodium sulphite are dissolved in 100 liters of distilled water and the pH adjusted to 8 with 6N hydrochloric acid. 1.6 liters of diacetyl-(2,3-butanedione) are added maintaining the pH at 8 by adding 6N hydrochloric acid.

The mixture is agitated for 10 minutes.

Separately, 4 kg of 2,4,5-triamino-6-hydroxy pyrimidine sulphate finely ground to $200\mu$ are suspended in 25 liters of distilled water.

The suspension obtained is added in small portions under agitation to the mixture prepared as stated above, maintaining the pH at 8 by adding 40% NaOH. The addition is completed in a time of about 15 minutes and the reaction then allowed to go to completion at ambient temperature and pH 8, in a time of about 1 hour.

An intense yellow precipitate forms and is filtered off carefully and washed with distilled water until sulphite disappears from the wash water.

The precipitate obtained is homogeneously redispersed in 100 liters of distilled water.

The dispersion is heated to boiling and $Na_2CO_3$ added slowly until a complete solution forms.

0.4 kg of activated carbon are added and the mixture filtered hot.

While keeping the solution at boiling point, the pH is adjusted to 8 with 6N HCl and the product allowed to crystallize at a temperature of 4° C.

It is filtered off, washed carefully with distilled water and dried under vacuum.

2.6 kg of yellow crystalline product is obtained which is insoluble in water but soluble in an aqueous alkaline environment.

On HPLC analysis (column: NUCLEOSIL SA 10μ 250×4 mm; eluent: 0.02M ammonium formate pH 4/20% methanol, flow 1 ml/min., U.V. detector 254 nm) the product shows a single peak with a retention time of 11.6 minutes.

The product ultraviolet spectrum shows an absorption maximum at 252 nm in 0.1N NaOH with $E_1\% = 1163$ (on dry substance).

On the average, the product is obtained with one molecule of water of crystallization.

| Elementary analysis: $C_8H_9N_5O \cdot H_2O$ | | | |
|---|---|---|---|
| | N | C | H |
| Calculated: | 33.48 | 45.93 | 5.30 |
| Found: | 33.54 | 46.02 | 5.25 |

EXAMPLE 2

Preparation of 2-amino-4-hydroxy pteridine (BR 468)

10 kg of anhydrous sodium sulphite are dissolved in 100 liters of distilled water and the pH adjusted to 7 with 6N hydrochloric acid. 3.6 liters of a 40% aqueous glyoxal solution are added maintaining the pH at 7 by adding 6N hydrochloric acid.

The procedure of Example 1 is followed but with the difference that during the reaction the pH is maintained at 7.

On termination of the reaction an intense yellow precipitate is obtained, filtered off and carefully washed with distilled water until sulphite disappears from the wash water.

This precipitate is homogeneously redispersed in 100 liters of distilled water.

The dispersion is heated until boiling and $Na_2CO_3$ added until a complete solution forms.

While keeping the solution boiling, the pH is adjusted with 6N hydrochloric acid up to the solubility limit (about pH 9).

The product is allowed to crystallize at a temperature of 4° C., washed carefully with distilled water and dried under vacuum.

2.2 kg of yellow crystalline product are obtained which is insoluble in water but soluble in an aqueous alkaline environment.

On HPLC analysis (column: NUCLEOSIL SA 10μ 250×4. mm; eluent: 0.02M ammonium formate pH 4/20% methanol, flow 1 ml/min., U.V. detector 254 nm) the product shows a single peak with a retention time of 8.7 minutes.

The product ultraviolet spectrum shows an absorption maximum at 251 nm in 0.1N NaOH with $E_1\% = 1257$ (on dry substance).

On the average, the product is obtained with 0.5 molecules of water of crystallization.

| Elementary analysis: $C_6H_5N_5O \cdot 0.5H_2O$ | | | |
|---|---|---|---|
| | N | C | H |
| Calculated: | 40.68 | 41.86 | 3.51 |
| Found: | 40.53 | 41.53 | 3.39 |

EXAMPLE 3

Preparation of 2,4-diamino-6,7-dimethyl pteridine (BR 474)

10 kg of anhydrous sodium sulphite are dissolved in 100 liters of distilled water and the pH adjusted to 8 with 6N hydrochloric acid. 1.6 liters of diacetyl-(2,3-butanedione) are added maintaining the pH at 8 by adding 6N hydrochloric acid.

The mixture is agitated for 10 minutes.

Separately, 4.1 kg of 2,4,5-tetraamino pyrimidine sulphate finely ground to 200μ are suspended in 25 liters of distilled water.

The suspension obtained is added in small portion under agitation to the mixture prepared as stated above, maintaining the pH at 8 by adding 40% NaOH.

The addition is completed in a time of about 15 minutes. The reaction mixture is heated to 60°–70° C. and the reaction then allowed to go to completion at this temperature in a time of about 1 hour.

An intense yellow precipitate forms and after cooling is filtered off and carefully washed with distilled water until sulphite disappears from the wash water. The precipitate obtained is homogeneously redispersed in 150 liters of distilled water and redissolved by adding HCl to pH 2.

0.4 kg of activated carbon are added and the mixture filtered.

The filtrate pH is adjusted to 8 with 40% NaOH to precipitate the product.

It is filtered off, washed carefully with distilled water and dried under vacuum.

2.5 kg of yellow crystalline product is obtained which is insoluble in water but soluble in dilute aqueous mineral acid solutions.

On HPLC analysis (column: NUCLEOSIL SA 10μ 250×4 mm; eluent: 0.02M ammonium formate pH 4/30% methanol, flow 1 ml/min., U.V. detector 254 nm) the product shows a single peak with a retention time of 12.6 minutes.

The product ultraviolet spectrum shows an absorption maximum at 244 nm in 0.1N HCl with $E_1\% = 840$ (on dry substance).

On the average, the product is obtained with 0.4 molecules of water of crystallization.

| Elementary analysis: $C_8H_{10}N_6O \cdot 0.4H_2O$ | | | |
|---|---|---|---|
| | N | C | H |
| Calculated: | 42.57 | 48.67 | 5.51 |
| Found: | 42.49 | 48.63 | 5.48 |

EXAMPLE 4

Preparation of 2-amino-6,7-dimethyl pteridine (BR 470)

The procedure described in Example 1 is followed but using 3.7 kg of 4,5,6-triamino pyrimidine sulphate instead of 2,4,5-triamino-6-hydroxy pyrimidine sulphate.

2.4 kg of yellow crystalline product is obtained which is insoluble in water but soluble in an aqueous alkaline environment.

On HPLC analysis (column: NUCLEOSIL SA 10μ 250×4 mm; eluent: 0.02M ammonium formate pH 4/20% methanol, flow 1 ml/min., U.V. detector 254 nm) the product shows a single peak with a retention time of 9.5 minutes.

| Elementary analysis: C₈H₉N₅ | | | |
|---|---|---|---|
| | N | C | H |
| Calculated: | 39.98 | 54.84 | 5.18 |
| Found: | 39.81 | 54.61 | 5.11 |

EXAMPLE 5

Preparation of 2,4-dihydroxy-6,7-dimethyl pteridine (BR 471)

The procedure described in Example 1 is followed but using 3.2 kg of 5,6-diamino-2,4-dihydroxy pyrimidine sulphate and heating to 60°–70° C. as in Example 3 instead of operating at ambient temperature.

2.1 kg of yellow crystalline product is obtained which is insoluble in water but soluble in an aqueous alkaline environment.

On HPLC analysis (column: NUCLEOSIL SA 10µ 250×4 mm; eluent: 0.02M ammonium formate pH 4/20% methanol, flow 1 ml/min., U.V. detector 254 nm) the product shows a single peak with a retention time of 10.4 minutes.

On the average the product is obtained with one molecule of water of crystallization.

| Elementary analysis: C₈H₈N₄O. H₂O | | | |
|---|---|---|---|
| | N | C | H |
| Calculated: | 26.66 | 45.71 | 4.80 |
| Found: | 26.73 | 45.92 | 4.87 |

EXAMPLE 6

Preparation of 4-hydroxy-6,7-dimethyl pteridine (BR 472)

The procedure described in Example 5 is followed but using 3.7 kg of 4,5-diamino-6-hydroxy pyrimidine sulphate.

2.4 kg of yellow crystalline product is obtained which is insoluble in water but soluble in an aqueous alkaline environment.

On HPLC analysis (column: NUCLEOSIL SA 10µ 250×4 mm; eluent: 0.02M ammonium formate pH 4/20% methanol, flow 1 ml/min., U.V. detector 254 nm) the product shows a single peak with a retention time of 9.1 minutes.

On the average the product is obtained with 0.2 molecules of water of crystallization.

| Elementary analysis: C₈H₈N₄O. 0.2H₂O | | | |
|---|---|---|---|
| | N | C | H |
| Calculated: | 31.17 | 53.45 | 4.71 |
| Found: | 31.03 | 53.38 | 4.65 |

EXAMPLE 7

Preparation of Tablets

| (a) | A 100 mg tablet contains: | |
|---|---|---|
| | 2-amino-4-hydroxy-6,7-dimethyl pteridine | 100 mg |
| | crosslinked carboxymethyl cellulose | 50 mg |
| | magnesium stearate | 10 mg |
| | microcrystalline cellulose to make up to | 400 mg |
| (b) | A 100 mg tablet contains: | |
| | 2,4-diamino-6,7-dimethyl pteridine | 100 mg |
| | corn starch | 80 mg |
| | polyvinylpyrrolidone | 20 mg |
| | magnesium stearate | 10 mg |
| (c) | A 100 mg tablet contains: | |
| | 2,4-dihydroxy-6,7-dimethyl pteridine | 100 mg |
| | sodium chloride | 50 mg |
| | polyvinylpyrrolidone | 20 mg |
| | corn starch to make up to | 400 mg |
| (d) | A 100 mg tablet contains: | |
| | 2-amino-4-hydroxy pteridine | 100 mg |
| | crosslinked carboxymethyl cellulose | 50 mg |
| | magnesium stearate | 10 mg |
| | microcrystalline cellulose to make up to | 400 mg |

EXAMPLE 8

Preparation of Capsules

| (a) | A 100 mg capsule contains: | |
|---|---|---|
| | 2-amino-4-hydroxy-6,7-dimethyl pteridine | 100 mg |
| | mannitol | 100 mg |
| | lactose | 100 mg |
| | magnesium stearate | 10 g |
| (b) | A 100 mg capsule contains: | |
| | 2,4-diamino-4-hydroxy-6,7-dimethyl pteridine | 100 mg |
| | mannitol | 100 mg |
| | lactose | 100 mg |
| | magnesium stearate | 10 g |

EXAMPLE 9

Preparation of Gastroresistant Tablets

| (a) | A 100 mg tablet contains: | |
|---|---|---|
| | 2-amino-4-hydroxy-6,7-dimethyl pteridine | 100 mg |
| | crosslinked carboxymethyl cellulose | 70 mg |
| | microcrystalline cellulose to make up to | 400 mg |
| | cellulose acetophthalate | 20 mg |
| | diethylphthalate | 6.4 mg |
| | silicone resin | 3.6 mg |
| (b) | A 100 mg tablet contains: | |
| | 2,4-diamino-6,7-diethyl pteridine | 100 mg |
| | crosslinked polyvinylpyrrolidone | 100 mg |
| | sodium chloride | 50 mg |
| | microcrystalline cellulose to make up to | 400 mg |
| | cellulose acetophthalate | 20 mg |
| | diethylphthalate | 20 mg |
| | silicone resin | 3.6 mg |
| (c) | A 100 mg tablet contains: | |
| | 2-amino-6,7-dimethyl pteridine | 100 mg |
| | sodium bicarbonate | 100 mg |
| | citric acid | 50 mg |
| | cellulose acetophthalate | 20 mg |
| | diethylphthalate | 6.4 mg |
| | silicone resin | 3.6 mg |

I claim:

1. A therapeutic process for treating memory and vigilance disturbance nature cognitive pathologies including Alzheimer-type senile dementia, multiinfarctual dementia, metabolic encephalopathies, Korsakoff's syndrome, and the consequences of the abuse of anxiolytic and neuroleptic therapies, said process comprising administering to a patient in need thereof a therapeutically effective amount of a pteridine of the formula

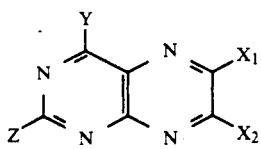

wherein Y and Z can be the same or different and are H, OH, or $NH_2$ and $X_1$ and $X_2$ can be the same or different and are OH, $C_1$–$C_4$ alkyl, phenyl, hydroxymethyl, or carboxyl.

2. The process of claim 1, wherein said pteridine is administered by injection.

3. The process of claim 1, wherein said pteridine is administered orally.

4. The process of claim 3, wherein said pteridine is administered in the form of a tablet, pill, capsule, sachet, or syrup.

* * * * *